United States Patent [19]

Saunders

[11] Patent Number: 4,483,882
[45] Date of Patent: Nov. 20, 1984

[54] PRESERVATION OF RELATIONSHIP OF PARTICLES AND SUPPORTING LIQUID OF A MONOLAYER DURING DRYING

[75] Inventor: Alex M. Saunders, San Carlos, Calif.

[73] Assignee: SmithKline Beckman Corporation, Philadelphia, Pa.

[21] Appl. No.: 518,953

[22] Filed: Aug. 1, 1983

[51] Int. Cl.³ .......................... A01N 1/02; B44D 1/02; G01N 1/28
[52] U.S. Cl. .......................................... 427/2; 424/3; 436/177
[58] Field of Search .................. 424/3; 427/2; 118/52; 436/177

[56] References Cited

U.S. PATENT DOCUMENTS 4,209,548  6/1980  Bacus ........................................ 427/2
4,305,722  12/1981  Kunz ................................... 427/2 X Primary Examiner—Michael R. Lusignan
Attorney, Agent, or Firm—Edward T. Lentz; Janice E. Williams; Alan D. Lourie

[57] ABSTRACT

Disclosed is a process of preparing blood spreads for microscopical examination wherein a smooth and homogeneous plasma layer is obtained. A combination of steps including timely fixation for the purpose of cell preservation, producing a cross-linked matrix in the plasma and performing of chemical reactions by diffusing reagents across an interface, are performed for the purpose of stabilizing both the cell shape and the smoothness and homogeneity of the plasma layer, while the fresh and still wet blood spread is immersed in a non-polar, water immisicible, solvent.

10 Claims, No Drawings

PRESERVATION OF RELATIONSHIP OF PARTICLES AND SUPPORTING LIQUID OF A MONOLAYER DURING DRYING

BACKGROUND OF THE INVENTION

1. Field of the Invention

The present invention relates, in general, to preparing blood spreads for microscopical examination and, in particular, to blood spreads having a smooth and homogeneous plasma layer. More specifically, this invention relates to a process comprising a combination of steps including timely fixation for the purpose of cell preservation, producing a cross-linked matrix in the plasma and performing of chemical reactions by diffusing reagents across an interface, for the purpose of stabilizing both the cell shape and the smoothness and homogeneity of the plasma layer, while the fresh and still wet blood spread is immersed in a non-polar solvent.

2. Description of the Prior Art

In the routine examination of blood for diagnostic purposes, it has been customary to spread a thin layer over the surface of a glass slide. A portion of the spread, referred to as a monolayer, is examined microscopically after a suitable process of staining which brings out contrast. Monolayer, in this context, is a reference to there being a single layer of cells without significant overlap. In the past, the plasma layer, which separates cells in this monolayer, has been acknowledged, but not regarded as having much importance either in the process of spreading the monolayer or in the subsequent analysis.

Three commonly-accepted methods of preparing blood spreads for microscopical examination are the Coverslip Method, the Wedge Smear Method and the Spinner Method. These are generally described in U.S. Pat. No. 4,209,548 as well as in U.S. Pat. Nos. 3,827,805 and 4,108,109. As described in U.S. Pat. No. 4,209,548, which teaches a method of vaporous fixation of the wet spread in the time between spreading and drying, there is a tendency to distort the shape of red blood cells during the process of drying the sample after formation of the monolayer by any means. This same patent also indicates in column 2, line 26, that cells would wash off the slide if the slide were dipped in a fixing solution before drying takes place. The process of vaporous fixation was also practiced by Adler, Saunders and Ornstein in a device described in a 1977 publication (Adler, S. L., Saunders, A., and Ornstein, L., "Fully Automated Preparation of High Quality Stained Blood Films," *Advances in Automated Analysis*, Mediad, Inc., Vol. I. 1977, pp. 77-80).

There are several disadvantages of preserving the shape of red blood cells by vaporous fixing of the monolayer. First, there are harmful effects on the shape of white blood cells which are not permitted to spread widely on the slide. Secondly, one is required to hold the slide in a vapor chamber for an extended amount of time. Since this chamber is the apparatus for making the monolayer, it is inoperable for a second specimen during processing of the first. Thirdly, the whole slide is necessarily exposed to the vapor and, hence, if the vapor is harmful to any part of the subsequent examination, a second slide must be prepared, excluding the vapor. Further, the vapor is toxic and therefore a health hazard unless carefully controlled.

During the performance of experiments on blood samples with artificially colored plasma, it was observed that the drying process involves variable degrees of migration of the plasma. This migration is best visualized by having the freshly prepared slide under microscopic observation while it is still wet. It is then possible to observe a timed sequence, in which the plasma layer appears smooth and homogeneous at first. Over a period of 15 seconds or less the colored plasma layer flows toward any proximal cell or particle. This migration stops when the specimen is dry. At this time it is possible to observe that the colored plasma has migrated to form rings around the cells or particles on the glass surface. Other portions of the colored plasma residue had formed irregular patterns between cells during the drying process.

By experiment it has been possible to show that changing the surface tension characteristics of the plasma provides some control over the degree of migration of colored plasma during the drying process. It was concluded that surface tension forces have a major influence during the drying process, both on the liquid plasma and on the shape of cells adherent to the slide.

Control of surface tension is possible by the addition of surface active agents prior to the application of blood to the slide. The surface active agents may be added either to the slide surface or to the blood. Such agents, however, also have a rapid and harmful effect on the surface membrane of cells and, therefore, cause a different and still unacceptable distortion of shape of both red blood cells and white blood cells.

Control of surface tension is also possible by immersing the slide while the spread sample is still wet. Since there is no surface, the forces are avoided. By immersing a still wet slide in a non-polar (non-water miscible) solvent such as cyclohexane, it has been possible to inhibit the migration of colored plasma for as much as 5 to 10 minutes. As the slide is removed from cyclohexane, however, and the solvent evaporates, the migration of colored plasma resumes and forms a ring around nearby cells or some irregular pattern. Thus, the process of distortion is retarded but not eliminated by simply immersing the wet slide in a nonmiscible (non-polar) solvent.

A process of cell embedding on the slide surface was described by L. Ornstein in "Technicon Autoslide Staining and Processing System," *Advances in Automated Analysis*, Mediad, Inc., Vol. I, 1977, pp. 81-82. In this process, however, the cells were already dry before infiltrating with an acrylic monomer and subsequently polymerizing with ultra violet light.

With respect to the action of a reagent across an interface, the synthesis of nylon, for example, to surround an aqueous droplet is practiced as one form of microencapsulation. For this purpose, the dispersed microdroplets of water contain the reagent hexamethylene diamine, while the non-polar solvent in which the microdroplets are dispersed may, for example, be a mixture of cyclohexane and chloroform. At the proper time during the dispersion process, the reagent sebacoyl chloride is added to the non-polar solvent. Reaction between the two active agents, hexamethylene diamine and sebacoyl chloride takes place at the interface between water and the non-polar solvent. The result is formation of a thin layer or membrane which completely surrounds the water droplets. Thickness can be controlled by concentration of the reagents and by time of reaction (See Immobilized Enzymes, CRC Press, 1973). However, when this process is performed on a wet blood film on a slide, the nylon formed by the reaction remains as a membrane at the interface. It covers but does not embed the cells and plasma and does not produce a matrix in the plasma layer.

It is, therefore, an object of this invention to provide a process of preparing blood spreads for microscopical examination which is devoid of the above-noted disadvantages.

It is another object of this invention to provide a process of preparing blood spreads wherein there is no distortion of the plasma layer during drying of plasma or of cell monolayers.

It is still another object of the present invention to provide a process of preparing blood films wherein the red blood cells and white blood cells are preserved in their original shape on the slide.

It is a further object of the present invention to provide a process of preparing blood films wherein both a smooth and undistorted plasma layer and cells without distortion are preserved.

SUMMARY OF THE INVENTION

The foregoing objects and others are accomplished in accordance with this invention, generally speaking, by providing a process comprising a combination of steps including (a) timely fixation (b) producing a cross-linked matrix in the plasma layer, (c) decreasing surface tension and retarding evaporation at the fresh blood spread by immersion in a non-polar (water immiscible) solvent, and (d) performing chemical reactions by diffusing reagents across an interface.

DETAILED DESCRIPTION OF THE INVENTION

According to the present invention, the four steps of (a) timely fixation for the purposes of cell preservation, (b) producing a cross-linked matrix in the plasma layer; (c) decreasing surface tension and retarding evaporation at the fresh blood spread by by immersion in a non-polar (water immiscible) solvent, and (d) performing a chemical reaction by diffusing reagents across an interface, are combined for the purpose of stabilizing both the cell shape and the smoothness and homogeneity of the plasma layer.

Distortion of the plasma layer during drying of cell monolayers is solved by producing the cross-linked matrix before drying. An agent for subsequent cross-linking in the plasma is dissolved in the plasma while the blood is still a liquid suspension. The activating or polymerizing agent is dissolved in the non-polar solvent. Concentrations are adjusted so that cross-linking occurs within about the first minute of immersion of the wet blood spread on the slide in the non-polar solvent while excessive reactions are prevented.

By proper adjustment of conditions of agent to be cross-linked, polymerizing agent, blood spreading process, non-polar solvent and time, one may separate two phenomena of distortion. First, by using a polymerizing agent which acts chiefly on the plasma component, migration of plasma during the subsequent drying is eliminated. In this case, the cells are left unaffected, except that surface tension forces as they would act on the cells are greatly reduced. The spreading or stretching of the cells after this treatment is intermediate between fixed cells and those without the treatment.

By using a polymerizing agent that also fixes the cells before they are dry, one may preserve both a smooth, undistorted plasma layer and cells without distortion. These cells generally have the appearance, after drying, of cells usually seen only in wet preparations. Loss of central palor in red blood cells as described in U.S. Pat. No. 4,209,548 does not happen under these conditions.

Any suitable cross-linking agent may be used in the process of the present invention. Typical cross-linking agents include formaldehyde, glutaraldehyde and trichloroacetic acid. Cross-linking action may be by structural change in the agent to be cross-linked, as with trichloroacetic acid, or by formation of additional covalent bonds, as with an aldehyde. While any suitable agent with these properties may be used, the agent of choice is glutaraldehyde.

Properties of the agent to be cross-linked include large molecular weight, solubility in the plasma of human blood, non-reactivity with either the plasma or particulate components of human blood, but responding to the cross-linking agent, and not causing cell aggregation or attachment of blood components to the cell surface. Optimum results were obtained by using human serum albumin as agent to be cross-linked and glutaraldehyde as a cross-linking agent.

Any suitable non-polar solvent may be used in the present invention. Properties of such a solvent include low surface tension, non-miscible with water but capable of dissolving the cross-linking agent, and non reactive with water, blood or the reagents used in cross-linking.

The optimum solvent used with glutaraldehyde and human serum albumin is cyclohexane.

Any suitable blood spreading process, such as the spinner process, the coverslip process and the wedge process, may be used in this invention, although it is preferred to employ the spinner process because a larger usable monolayer area is produced.

The following examples further define the present invention. It should be noted, however, that these examples are intended to illustrate, and in no way are intended to limit the invention.

EXAMPLE I

The agent, used herein, for subsequent cross-linking is human serum albumin, the coloring agent is a dye Fast Green SF (color index #42053), the slide preparation is by a spinner process described in U.S. Pat. No. 3,827,805, the non-polar solvent is cyclohexane and the cross linking or activating agent dissolved in cyclohexane is glutaraldehyde. Human serum albumin (HSA) is a 30% aqueous solution. Glutaraldehyde solution is 1/6 of the maximum or saturation concentration in cyclohexane. It is prepared by shaking together a 25% aqueous glutaraldehyde solution and the pure cyclohexane at room temperature. Subsequently, the saturated solution is diluted with pure cyclohexane in ratio of about 1 part in 6. Two parts of blood are mixed with one part of Human Serum Albumin solution. A monolayer spread is made on the slide using a spinner and is immediately immersed in cyclohexane glutaraldehyde. After 30 seconds, the slide is transferred to pure (clean) cyclohexane where the unreacted glutaraldehyde is rinsed away. Upon removal of the slide from the clean cyclohexane bath, the solvent is permitted to evaporate and the slide is dried.

Both plasma and cells are preserved, free of distortion from their original shape.

EXAMPLE II

Example I is repeated using trichloracetic as the cross-linking agent for the human serum albumin. Immersion of the wet blood film is kept down to about 15 seconds in cyclohexane containing about 1/100% of trichloroacetic acid. The cross-linking agents, as in Example I, above, acts by crossing the boundary between the non-polar solvent and the water wet monolayer of blood, and by performing its cross-linking chemical reaction after further diffusion on the water side of the boundary. Among other reactions the trichloroacetic acid causes denaturation of the albumin which then precipitates in place to the extent that a smooth plasma layer is obtained. In this example, only plasma is preserved free of distortion. Since trichloroacetic acid does not fix the cells, they are subjected to stretching forces during drying. As a result they resemble cells as they would appear in conventional monolayer blood spreads.

While specific components of the present system are defined in the examples above, many other variables may be introduced which may in any way affect, enhance or otherwise improve the invention. These are intended to be included herein.

While variations are given in the present application, many modifications and variations will occur to those skilled in the art upon reading the present disclosure. These, too, are intended to be included herein.

What is claimed is:

1. A process of preparing blood films for microscopical examination wherein the cell shape, smoothness and homogeneity of the plasma layer are stabilized, which comprises a combination of steps including (a) timely fixation; (b) producing a cross-linked matrix in the plasma; (c) immersing the blood film, while still wet, in a non-polar solvent to control surface tension and evaporation rate; and (d) performing chemical reactions by diffusing chemical reagents across an interface between the non-polar solvent and the blood.

2. The process of claim 1 wherein an agent to be cross-linked is dissolved in the plasma while the blood is still in liquid suspension.

3. The process of claim 2 wherein said agent to be cross-linked is human serum albumin.

4. The process of claim 1 wherein a cross-linking agent is selected from the group consisting of formaldehyde, glutaraldehyde, trichloroacetic acid, and mixtures thereof.

5. The process of claim 4 wherein said cross-linking agent is glutaraldehyde.

6. The process of claim 3 wherein said non-polar solvent has the properties of having low surface tension, being non-miscible with water but capable of dissolving said cross-linking agent and being non-reactive with water, blood or the reagents used in cross-linking.

7. The process of claim 6 wherein said non-polar solvent is cyclohexane.

8. The process of claim 1 wherein human serum albumin is the agent to be cross-linked and glutaraldehyde is used as the cross-linking agent.

9. The process of claim 8 wherein the solvent is cyclohexane.

10. The process of claim 1 wherein the spinner process is employed to spread a thin layer of blood over a slide.

* * * * *